United States Patent [19]
Bowen

[11] Patent Number: 5,966,203
[45] Date of Patent: Oct. 12, 1999

[54] VACUUM EASEL

[76] Inventor: Michael L. Bowen, 6901 Glenlake Pkwy., Apt. #6873C, Atlanta, Ga. 30328

[21] Appl. No.: 09/026,751

[22] Filed: Feb. 20, 1998

Related U.S. Application Data

[63] Continuation-in-part of application No. 08/608,118, Feb. 28, 1996, Pat. No. 5,827,246.

[51] Int. Cl.$^6$ .............................. G03B 27/60; G03B 27/62
[52] U.S. Cl. ................................................. 355/73; 355/76
[58] Field of Search ................................. 355/73, 75, 74, 355/77, 76; 396/441; 604/313–317; 137/602

[56] References Cited

U.S. PATENT DOCUMENTS

| | | | |
|---|---|---|---|
| 3,077,141 | 2/1963 | Wanielista et al. | 355/73 |
| 3,157,101 | 11/1964 | Rabinow | 396/441 |
| 3,413,903 | 12/1968 | Maldarelli | 396/441 |
| 3,520,300 | 7/1970 | Flower | 128/276 |
| 3,572,228 | 3/1971 | Ternes | 396/441 |
| 3,610,751 | 10/1971 | Miyauchi | 355/73 |
| 3,783,863 | 1/1974 | Kliever | 128/134 |
| 3,813,682 | 5/1974 | Nishikawa et al. | 396/441 |
| 3,929,135 | 12/1975 | Thompson | 128/287 |
| 4,175,857 | 11/1979 | Rapp et al. | 355/73 |
| 4,248,651 | 2/1981 | Kojimoto et al. | 156/198 |
| 4,525,166 | 6/1985 | Leclerc | 604/133 |
| 4,533,352 | 8/1985 | Van Beek et al. | 604/317 |
| 4,679,580 | 7/1987 | Devall et al. | 137/39 |
| 4,679,590 | 7/1987 | Hergenroeder | 137/602 |
| 4,729,404 | 3/1988 | Hergenroeder | 137/602 |
| 4,760,928 | 8/1988 | Bustos | 211/59.4 |
| 4,791,459 | 12/1988 | Hoffman | 355/91 |
| 4,803,813 | 2/1989 | Fiterman | 52/199 |
| 4,828,894 | 5/1989 | Taylor | 428/53 |
| 4,984,017 | 1/1991 | Nishida et al. | 355/91 |
| 5,014,389 | 5/1991 | Ogilvie | 15/353 |
| 5,034,006 | 7/1991 | Hosoda et al. | 604/317 |
| 5,176,667 | 1/1993 | DeBring | 604/356 |
| 5,192,276 | 3/1993 | Gatti | 604/313 |
| 5,215,539 | 6/1993 | Schoolman | 604/280 |
| 5,304,056 | 4/1994 | Fetterhoff | 425/304 |
| 5,346,264 | 9/1994 | Law et al. | 285/158 |
| 5,380,278 | 1/1995 | Mombrinie | 604/35 |
| 5,414,491 | 5/1995 | Bryant | 355/73 |
| 5,437,651 | 8/1995 | Todd et al. | 604/313 |
| 5,484,427 | 1/1996 | Gibbons | 604/313 |
| 5,486,932 | 1/1996 | Leonard | 358/498 |
| 5,549,584 | 8/1996 | Gross | 604/313 |
| 5,563,683 | 10/1996 | Kamiya | 355/53 |
| 5,827,246 | 10/1998 | Bowen | 604/313 |

OTHER PUBLICATIONS

*Kull & Company Photo Systems*, "The Airboard™ Vacuum Easel" (one page), Jun. 30, 1997.
*NASA Tech Brief*, "Copyboard Quickly Makes Clean Printing Plates" (one page), 1985.
*Photo Techniques*, Jul./Aug. 1997, "Vacuum Easel" (one page).
*Lyn Associates Catalog*, "The Cobra–Pro 21"×25" Vacuum Easel" (six pages), No date.
Visipore Federal Trademark Registration.
Hydroknit Federal Trademark Registration.

*Primary Examiner*—D. Rutledge
*Attorney, Agent, or Firm*—Baker & Botts, L.L.P.

[57] ABSTRACT

Vacuum easel for releasably holding material. The vacuum easel includes a panel having a first sheet and a second sheet with a plurality of walls disposed between the first and second sheets. The walls define a series of progressively larger air pathways between the first and second sheets. A plurality of openings are formed in the first sheet to allow communication of air between the exterior of the first sheet and the respective air pathways. At least a subset of the openings are associated with each of the air pathways. A zone selector is operable to selectively communicate a source of vacuum with at least one of the air pathways to draw air from the exterior of the vacuum easel through the openings associated with the selected air pathway.

32 Claims, 4 Drawing Sheets

VACUUM EASEL

RELATED APPLICATIONS

This application is a continuation-in-part application based on patent application Ser. No.08/608,118 filed Feb. 28, 1996 entitled "Vacuum Pad for Collecting Potentially Hazardous Fluids," now U.S. Pat. No. 5827,246.

TECHNICAL FIELD OF THE INVENTION

This invention relates in general to the field of photographic and art equipment. In particular, this invention relates to a vacuum easel formed from a corrugated panel for use in releasably holding paper, photographic film or other types of flat, thin sheets of material on a generally smooth working surface.

BACKGROUND OF THE INVENTION

Vacuum easels are well known in the photographic arts for releasably holding a sheet of paper, photographic film or other flat material. Conventional easels are relatively thick and provide a relatively uniform vacuum over the entire surface of the easel. The thickness of the easel limits the size of prints that can be made with an enlarger disposed over the easel because it reduces the maximum separation distance between the enlarger and a sheet of paper held by the easel on which the print is to be made. The uniform vacuum of the easel is also problematic when used to hold a sheet of material that does not cover the entire easel. This is because the force exerted on the smaller sheet of material is substantially lowered due to it the lack of resistance in pulling air through parts of the easel that are not covered by the material. As a result, the easel cannot hold the sheet of material with enough strength as may be desired.

An additional problem with conventional easels is the inability to place successive sheets of material in the exact same location on the easel. For example, with photographic film printing, multiple prints cannot be made from the same negative without readjusting the equipment if subsequent sheets of photographic paper cannot be placed exactly where the first one was placed when the original adjustments were made.

Other problems with conventional easels include the tendency of some sheets of material to "curl up" when placed on the surface of the easel and the tendency of the easel to become warped. Such curling of material or warpage of the easel results in a print made on the easel being distorted. To prevent such distortion, Applicant has, more than one year prior to the filing date of the present application, but after the filing date of the parent application, sold a vacuum easel including a corrugated panel sandwiched between stiff supporting structures. Corrugated plastic panels and boards have been satisfactorily used for a wide variety of products as represented by U.S. Pat. No. 4,760,928, entitled "Corrugated Sheet Plastic Beverage Display Case;" U.S. Pat. No. 4,803,813 entitled, "Foldable Corrugated Plastic Roof Ventilator," and U.S. Pat. No. 4,828,894, entitled "Corrugated Plastic Board Assemblies." Also, various processes are well known to form a wide variety of articles from corrugated plastic material. U.S. Pat. No. 4,428,651, entitled "Thermal Forming Process of Corrugated Plastic Board" discloses one example of these processes. U.S. Pat. No. 5,304,056, entitled "Apparatus for Sealing Edges of Corrugated Plastic Material" provides further examples of fabricating techniques using corrugated plastic material. Each of the preceding patents is incorporated by reference for all purposes within this application.

Although the vacuum easel with supporting structures reduces warping and thicknesses associated with conventional easels, it did not provide sufficient force to hold smaller sheets of material, permit successive sheets of material to be placed in the same location as the original or prevent air flow around edges of the sheet of material to allow the sheet to remain flat on the easel surface.

SUMMARY OF THE INVENTION

In accordance with teachings of the present invention, disadvantages and problems associated with previous equipment and methods for releasably holding material on a flat surface have been substantially reduced or eliminated. The present invention provides a vacuum easel including a corrugated panel having a first sheet and a second sheet with a plurality of walls disposed between the sheets. The walls define a series of progressively larger pathways between the first and second sheets. A plurality of openings are formed in the first sheet to allow communication of air between the exterior of the first sheet and the respective air pathways. At least a subset of the openings are associated with each of the air pathways. A zone selector is operable to selectively communicate a source of vacuum with at least one of the air pathways to draw air from the exterior of the vacuum easel through the openings associated with the selected air pathway.

More specifically, in accordance with one embodiment of the present invention, the zone selector comprises a manifold coupled to the air pathways. An air barrier is operable to be positioned in the manifold to selectively communicate the source of vacuum with at least one of the air pathways to draw air from the exterior of the vacuum easel through the openings associated with the selected air pathways. In this embodiment, the air barrier may comprise a plurality of zoning rods operable to slide into opposing ends of the manifold to selectively communicate the source of vacuum with at least one of the air pathways.

Technical advantages of the present invention include providing a relatively thin vacuum easel, which may be easily adapted to various geometric configurations. The vacuum easel can be attached to a source of low level vacuum, such as a home vacuum cleaner, and used in a photographic laboratory to hold photographic film and photographic paper during the process of developing and printing pictures. The thinness provided in this embodiment of the present invention is advantageous for use with an enlarger as the vacuum easel's size will leave extra height room for the enlarger.

Another technical advantage of the present invention includes providing a zoning system that allows the user to select the size of the zone through which air will flow. In particular, the zoning system confines the vacuum to a selected zone or set of zones, which allows the easel to insert a stronger force on smaller sheets of material placed on the easel.

Yet another technical advantage of the present invention includes fabricating the vacuum easel from relatively low cost corrugated material, such as a corrugated plastic panel. In addition to the relatively low cost, the corrugated plastic panel is relatively strong and not easily crushed or warped. This is especially advantageous for uses involving the process of developing and printing photographs because easels which can warp or deform easily may cause distortion in the photograph.

Other technical advantages of the present invention will be readily apparent to one skilled in the art from the following figures, descriptions, and claims.

BRIEF DESCRIPTION OF THE DRAWINGS

For a more complete understanding of the present invention and the advantages thereof, reference is now made to the following written description taken in conjunction with the accompanying drawings, in which.

DETAILED DESCRIPTION OF THE INVENTION

The preferred embodiments of the present invention and their advantages are best understood by referring to FIGS. 1–6 of the drawings, where like numerals are being used for like and corresponding parts of the various drawings.

Figure 1:
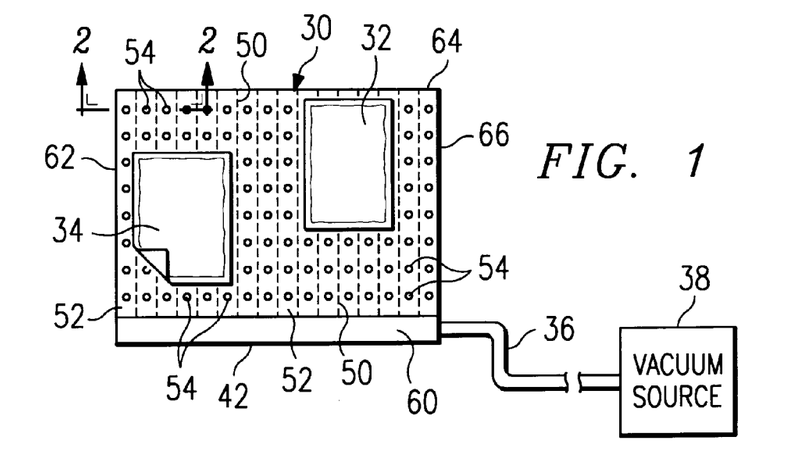
FIG. 1 is a schematic drawing showing a vacuum easel attached to a vacuum source for holding one or more sheets of material.

FIG. 1 illustrates a vacuum easel 30 attached to a vacuum source 38 by a conduit 36. The vacuum easel 30 may be used in photographic film developing laboratories and other developing and printing environments to hold one or more sheets of material 32 and 34. The material 32 and 34 may be paper, photographic film or any other flat material.

The vacuum easel 30 includes a corrugated panel 40 and a manifold 42. The corrugated panel 40 may be formed of plastic and also be referred to as a corrugated plastic board. Other types of corrugated material having desired characteristics of easy manufacture and assembly along with air flow channels may be satisfactorily used to form vacuum easel 30. Wax coated cardboard is an example of another type of corrugated material satisfactory for use with the present invention.

Corrugated panels formed from polypropylene are often available at relatively low cost when purchased in large quantities. Various thermoplastic polymers in addition to polypropylene may be used to form corrugated panels satisfactory for use with the present invention. Corrugated plastic panels satisfactory for use with the present invention may be obtained from various sources. One source is Coroplast, Inc., located at 4501 Spring Valley Rd., Dallas, Tx. Corrugated plastic panels are available in a wide variety of colors and can easily be formed into various geometric configurations as required for each application.

Figure 2:
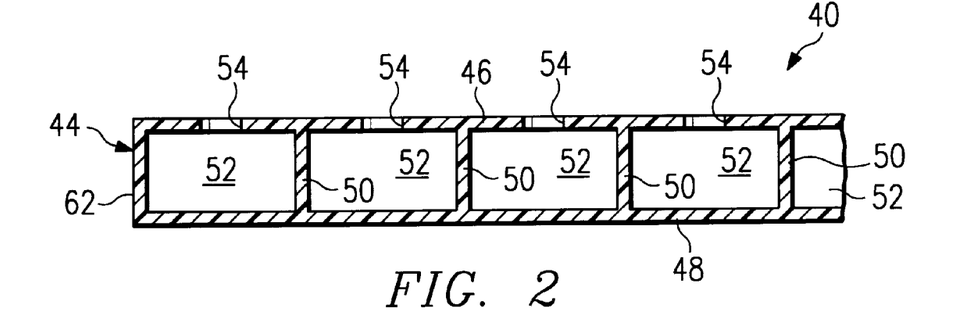
FIG. 2 is a drawing in section with portions broken away of the vacuum easel taken along lines 2—2 of FIG. 1.

FIG. 2 illustrates a cross-section of the corrugated panel 40. Referring to FIGS. 1–2, the corrugated panel 40 includes a first sheet 46 and second sheet 48 with a plurality of corrugated ribs 50 disposed therebetween. First sheet 46, second sheet 48 and corrugated ribs 50 are formed as integral parts of corrugated panel 40. A plurality of air flow channels 52 are formed between first sheet 46 and second sheet 48 by respective corrugated ribs 50. A plurality of openings 54 are formed in first sheet 46 to allow air communication between the exterior of vacuum easel 30 and respective air flow channels 52. Second sheet 48 preferably provides an air impervious barrier in order to allow the vacuum to function efficiently even if openings exist in second sheet 48 corresponding to openings 54 in first sheet 46.

The number, the size and the location of each opening 54 in first sheet 46 may be varied depending upon the intended application for the resulting vacuum easel 30. For example, FIGS. 1–2 show each opening 54 having a generally circular configuration uniformly spaced with respect to each other. For some applications, openings 54 may be slots or slits as compared to circular openings. Also, the number of openings 54 may be concentrated in one or more portions of first sheet 46 or may be uniformly spaced with respect to each other. Preferably, more than one opening 54 will be formed in first sheet 46 for each air flow channel 52. Providing multiple openings 54 in each air flow channel 52 tends to improve the air flow therethrough.

Openings 54 may be formed from various types of sharp piercing tools and/or drills depending upon the specific type of material used to form corrugated panel 40. During the fabrication of vacuum easel 30 from one or more relatively thin (one to twenty millimeters thick) corrugated panels 40, care must be taken to ensure that the residue from forming the openings 54 does not block or obstruct air flow in the respective air flow channels 52.

As shown in FIGS. 1–2, vacuum easel 30 has a generally rectangular configuration defined in part by first edge 60, second edge 62, third edge 64 and fourth edge 66. As best shown in FIG. 2, each air flow channel 52 preferably extends longitudinally from third edge 64 to first edge 60. Manifold 42 is attached to and forms a part of first edge 60. For many applications, corrugated panel 40 will preferably have a thickness in the range of one millimeter to twenty millimeters.

One of the benefits of using the corrugated plastic panel 40 to form vacuum easel 30 includes the ability to seal the ends of the air flow channels 52 opposite from manifold 42 along third edge 64. This feature of corrugated plastic panels or corrugated plastic board is described in more detail in U.S. Pat. No. 5,304,056. The perimeter of corrugated panel 40 can be easily heat sealed to prevent undesired air flow along the perimeter of the corrugated panel 40. This forms a generally air impervious enclosure around the perimeter of the corrugated panel between the first sheet 46 and the second sheet 48. One embodiment may include sealing the entire perimeter, while other embodiments use a frame in connection with unsealed edges.

As best shown in FIG. 2, air flow channels 52 are disposed adjacent to each other extending laterally from fourth edge 66 to second edge 62. Corrugated ribs 50 direct air flow from openings 54 longitudinally through the associated air flow channel 52 to manifold 42. Corrugated ribs 50 prevent air flow laterally between adjacent air flow channels 52.

Depending upon the intended application, air flow channels 52 may be formed in a corrugated panel 40 having cross-sections other than a generally rectangular configuration as shown in FIG. 2. For example, air flow channels 52 may be formed by corrugated ribs 50 having a generally sanusoidal or wavy configuration between first and second sheets 46 and 48. In these and other embodiments, the corrugated ribs 50 operate to return the associated air flow channels 52 to their original configuration after being deformed. Thus, the top of the vacuum easel 30 may remain substantially flat and undeformed even after extensive use.

The top of the vacuum easel 30 may be further strengthened by providing additional structure such as a stiff sheet of material outwardly of the first sheet.

The manifold 42 is open to the air flow channels 52 to provide an air collection chamber. In operation, air is drawn from the exterior of the vacuum easel 30 through the openings 54 into the air flow channels and collected in the manifold 42. As used herein, the term "air" includes any type of gaseous or similar medium. From the manifold 42, the collected air is drawn through the conduit 36 by the vacuum source 38.

For some applications, the conduit 36 may be a flexible hose to accommodate varying the location of the vacuum easel 30. In other applications, the conduit 36 may be part of a fixed network of tubing. Vacuum source 38 may be a wall suction port for supplying a relatively low level suction for approximately three hundred milliliters of mercury below atmospheric pressure. Alternatively, vacuum source 38 may be a portable blower, such as a home vacuum cleaner, that can be easily moved to various locations within the facility. A wide variety of fittings and connections may be used to attach the conduit 36 with manifold 42 and vacuum source 38.

FIGS. 3–6 illustrate a vacuum easel 110 in accordance with another embodiment of the present invention. In this embodiment, as described in more detail below, the vacuum easel 110 includes a zoning system to releasably hold different sized sheets of material.

Figure 3:
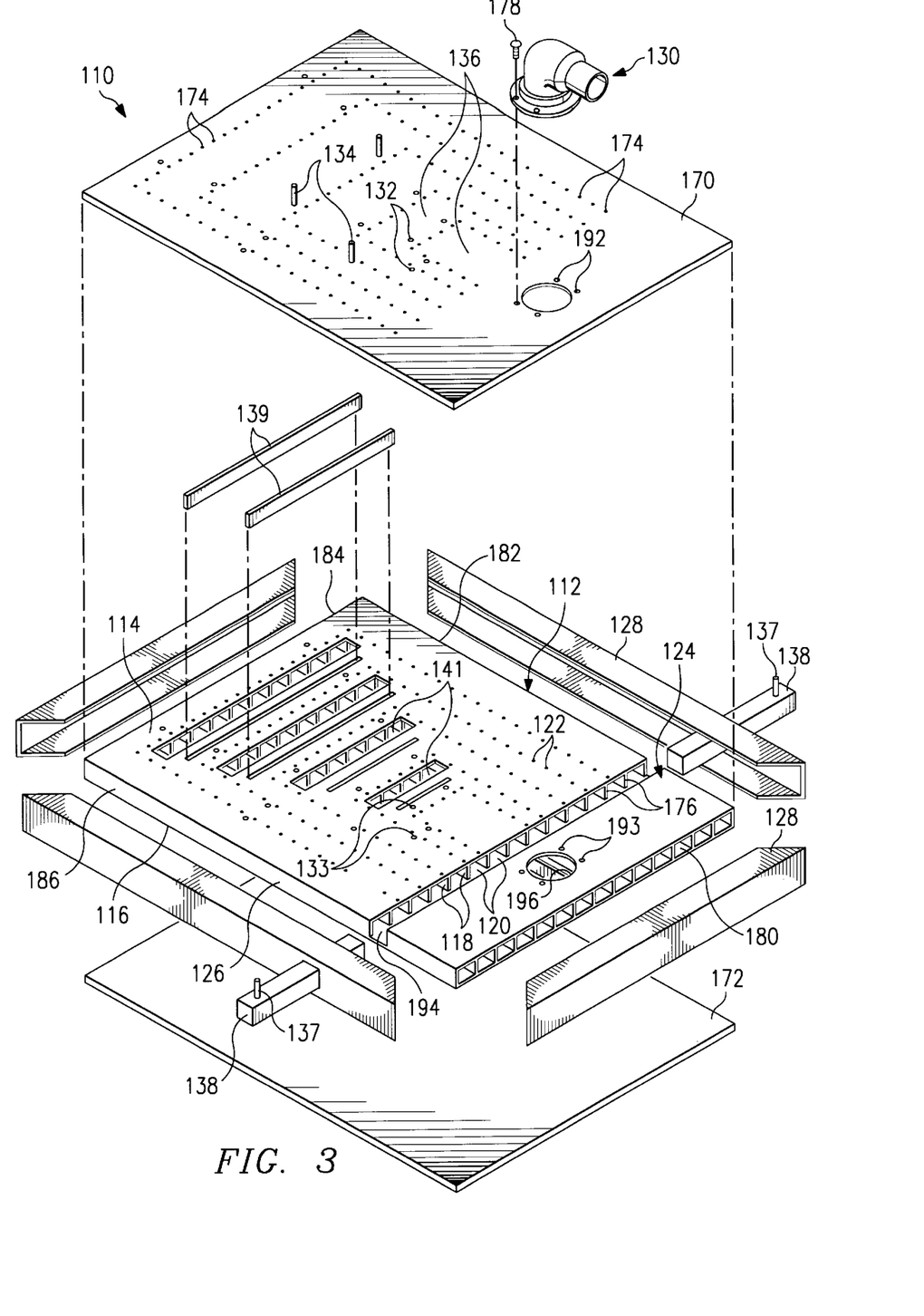
FIG. 3 is an exploded view of a vacuum easel having a plurality of zones and a zone selector for holding different sized sheets of material.

Referring to FIG. 3, vacuum easel 110 includes corrugated panel 112 with conduit 130, frame 128, air barriers 138, first structure 170 and second structure 172. Corrugated panel 112 includes manifold 124. One end of conduit 130 is coupled to and provides air communication with manifold 124. The other end of conduit 130 is attached to a vacuum source (not expressly shown) as previously described in connection with vacuum easel 30. As will be described in more detail below, coupling vacuum easel 110 with a vacuum source allows sheets of material 143 to be releasably held on the surface of the vacuum easel 110.

The corrugated panel 112 is similar to the corrugated plastic panel 40 used to fabricate the vacuum easel 30. The corrugated panel 112 includes a first sheet 114 and a second sheet 116 with a plurality of corrugated ribs 118 disposed therebetween. First sheet 114, second sheet 116 and corrugated ribs 118 are formed as integral parts of the corrugated panel 112. A plurality of air flow channels 120 are formed between first sheet 114 and second sheet 116 by respective corrugated ribs 118. A plurality of openings 122 are formed in the first sheet 114 to allow air communication between the exterior of the vacuum easel 110 and respective air flow channels 120. The openings 122 may be formed as previously described in connection with openings 54 of vacuum easel 30. Second sheet 116 preferably provides an air impervious barrier in order to allow the vacuum to function efficiently even if openings exist in the second sheet 116 corresponding to openings 122 in first sheet 114.

The number, the size and the location of the openings 122 in the first sheet 114 may be varied depending on the intended application for the resulting vacuum easel 110. For example, FIGS. 3–6 show each opening 122 having a generally circular configuration and show the openings arranged in a plurality of zones 136. As previously described in connection with openings 54, openings 122 may be formed from various types of sharp piercing tools and/or drills depending upon the specific type of material used to form corrugated panel 112. As also previously described in connection with openings 54, for some applications, openings 122 may be slots or slits as compared to circular openings.

As shown in FIGS. 3–6, vacuum easel 110 has a generally rectangular configuration defined in part by first edge 180, second edge 182, third edge 184 and fourth edge 186. As best shown in FIG. 3, each air flow channel 120 preferably extends longitudinally from third edge 184 to first edge 180. Manifold 124 is attached to and forms a part of first edge 180. For many applications, corrugated panel 112 will preferably have a thickness in the range of one millimeter to twenty millimeters. As best shown by FIG. 3, air flow channels 120 are disposed adjacent to each other extending laterally from fourth edge 186 to second edge 182. Corrugated ribs 118 direct air flow from openings 122 longitudinally through the associated air flow channel 120 to manifold 124. Corrugated ribs 118 prevent air flow laterally between adjacent air flow channels 120.

As shown in FIG. 3, manifold 124 may comprise a slot 194 formed between ends 176 and first edge 180 of corrugated panel 112. Slot 194 extends laterally from fourth edge 186 to second edge 182. A hole 196 in first sheet 114 allows conduit 130 to be coupled to air flow channels 120 underneath hole 196. Slot 194 allows communication of air between air flow channels 120 underneath hole 196 and air flow channels 120 which extend from third edge 184 to ends 176.

Vacuum source draws air from the exterior of vacuum easel 110 by means of conduit 130. As previously described in connection with conduit 36, conduit 130 may be a flexible hose to accommodate varying the location of vacuum easel 110 relative to the vacuum source or part of a fixed network of tubing and hoses. A wide variety of fittings and connections may be used to couple conduit 130 to manifold 124. In one embodiment, as shown in FIG. 3, a set of four screws 178 attach conduit 130 to manifold 124 through apertures 192 and first structure 170 and/or apertures 193 and first sheet 114.

As previously described in connection with corrugated panel 40, corrugated panel 112 can be easily heat sealed to prevent undesired air flow along the perimeter of the corrugated panel 112. This forms a generally air impervious enclosure 126 around the perimeter of the corrugated panel 112 between the first sheet and the second sheet 114 and 116. One embodiment includes sealing the entire perimeter, while another embodiment, as shown in FIG. 3, allows first edge 180 to remain unsealed. In this embodiment, frame 128 is formed around the perimeter of vacuum easel 110. This frame is generally necessary if first edge 180 is not sealed in order to set u a vacuum inside vacuum easel 110. Otherwise, frame 128 may be used for cosmetic purposes and for structural purposes, to protect vacuum easel 110 during shipping and operation.

Depending upon the capacity of the vacuum source attached to manifold 124, vacuum easel 110 may function satisfactorily even though a defect such as a split or opening may occur along edges 180, 182, 184 and/or 186, as long as sufficient vacuum can be maintained within air flow channels 120 to draw air into manifold 124. One of the benefits of the present invention is that vacuum easel 110 may continue to function satisfactorily despite minor damage and/or abuse to corrugated panel 112.

Figure 4:
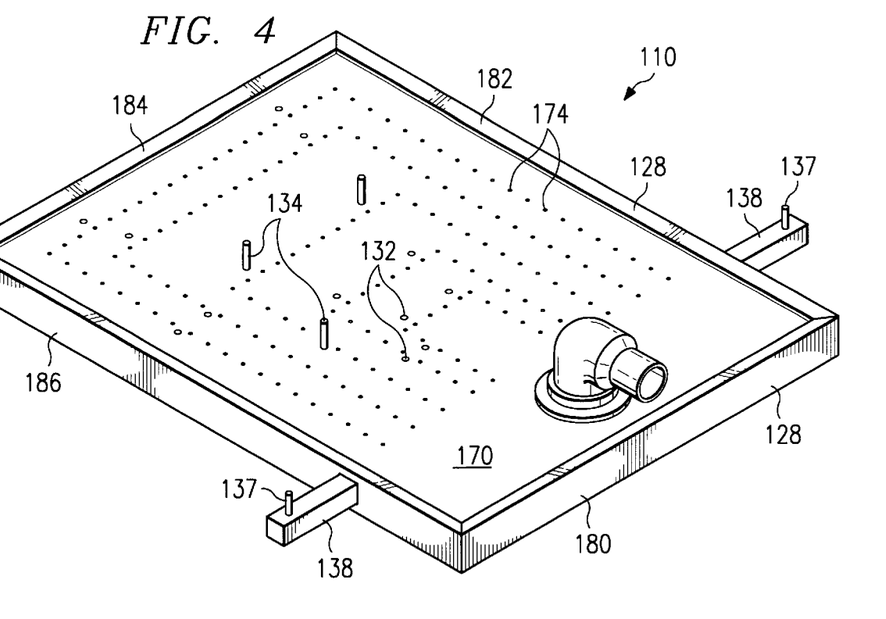
FIG. 4 is a schematic drawing showing the vacuum easel of FIG. 3 in assembled form.
Figure 5:
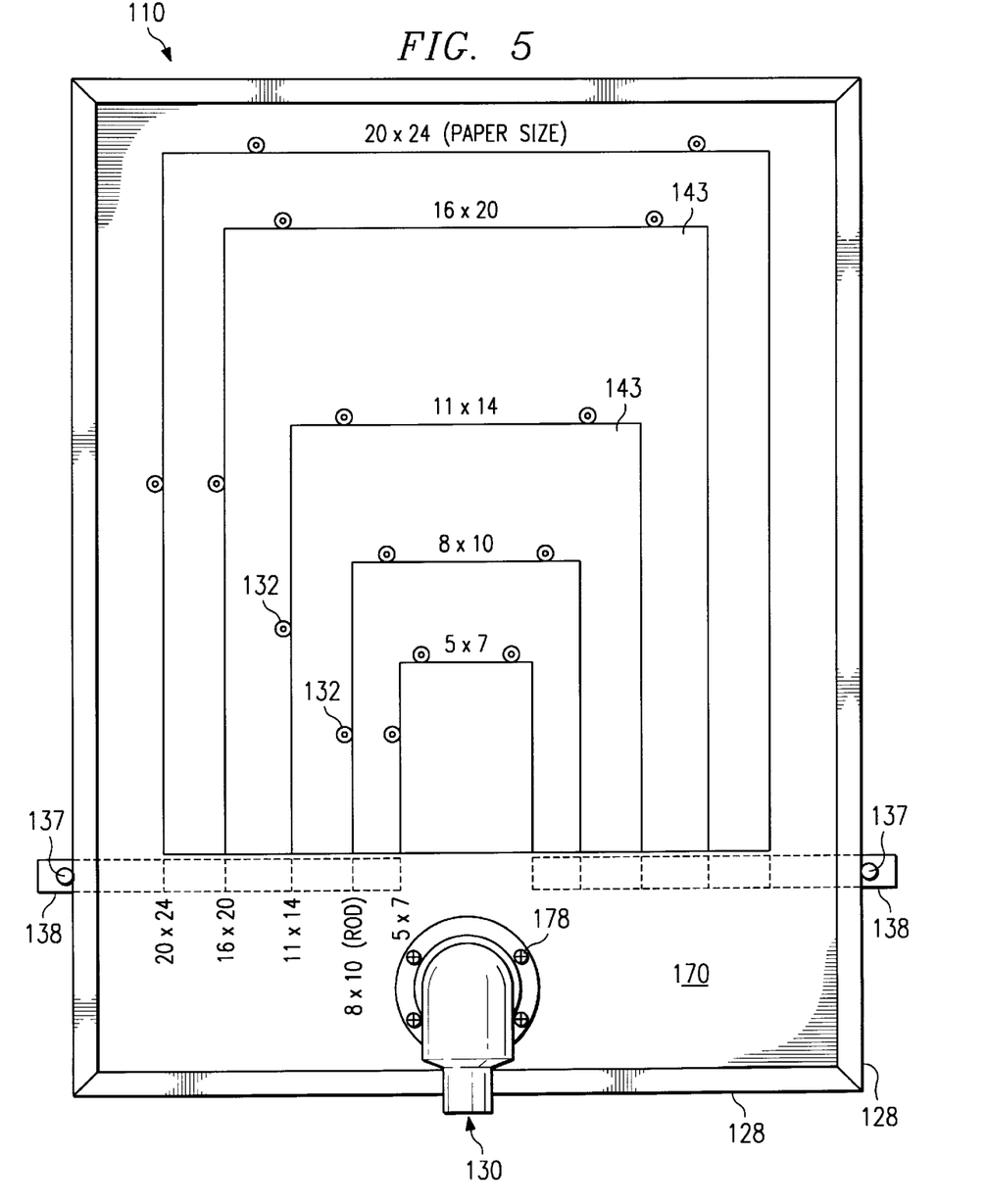
FIG. 5 is a top plan view of the vacuum easel pictured in FIGS. 3–4, showing different sized sheets of material aligned with registration pins on the vacuum easel and further showing the configuration of the zone selector.

As shown in FIGS. 3–5, air barriers 138 may be selectively positioned in slot 194 to communicate the source of vacuum with openings 122 of a selected zone 136 to draw air from the exterior of vacuum easel 110 through openings 122 of the selected zone 136. In one embodiment, two air barriers 138 are used on opposing sides of slot 194. The vacuum source is available only to the zone 136 which has been selected by placement of air barriers 138 within slot 194. When air barriers 138 are fully inserted, the smallest zone 136 is selected. Stop pins 137 may be placed on the ends of air barriers 138 to prevent air barriers 138 from being inserted too far. As the air barriers 138 are withdrawn, the vacuum source becomes available to additional air flow channels 120 corresponding to larger zones 136.

An alternative embodiment includes different sets of air barriers 138, each sized to fit a particular zone 136 when fully inserted. Also, different zones 136 could be selected using only one air barrier 138 by positioning the zones 136 against one side of the corrugated panel 112, instead of positioning the zones 136 in the middle of the corrugated panel 112.

As shown in FIG. 3, each zone 136 is formed by three different sides, with the fourth side for each being the manifold 124. Communication of air between manifold 124 and certain air flow channels 120 is blocked by air barriers 138. Corrugated ribs 118 which are lined up with air barriers 138, therefore, form two of the sides of each zone 136. The third side is formed by divider 139 placed across at least one air flow channel 120, with the exception of the largest possible zone which makes use of the sealed third edge 184 as a third side.

For each zone 136 except the smallest zone 136, a transverse channel 141 is formed in the section of air flow channels 120 blocked by the divider 139 associated with the next smallest zone 136. This allows communication of air between manifold 124 and air flow channels 120 which would otherwise be prevented by divider 139.

The embodiment of the present invention shown in FIGS. 3–5 includes corrugated panel 112 disposed between first structure 170 and second structure 172. First structure 170 is disposed adjacent to first sheet 114 of corrugated panel 112 and second structure 172 is disposed adjacent to second sheet 116 of corrugated panel 112. A plurality of openings 174 formed in first structure 170 communicate through openings 122 in first sheet 114 with the source of vacuum to releasably hold a sheet of material 143 on first structure 170. In this embodiment, first structure 170 and second structure 172 are formed from relatively hard, stiff material as compared to corrugated panel 112. In addition, first structure 170 provides a generally smooth exterior surface for vacuum easel 110.

Another aspect of the present invention includes a plurality of recesses 132, as shown in FIGS. 3–5, which receives a plurality of registration pins 134 to align sheets of material 143 with openings 122 making up different zones 136. In accordance with one embodiment, recesses 132 are formed in first structure 170 and registration pins 134 may be inserted into recesses 132. However, in another embodiment, recesses 133 may be formed in first sheet 114. If first structure 170 is not used, registration pins 134 may be inserted into recesses 133 in first sheet 114. In addition, even with first structure 170 in place, registration pins 134 may be inserted into recesses 132 in first structure 170 and extend down into recesses 133 in first sheet 114.

Figure 6:
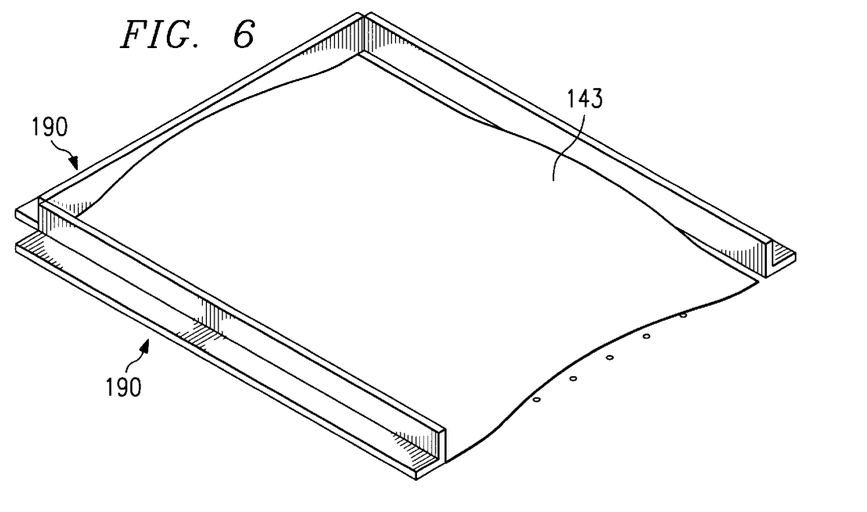
FIG. 6 is a schematic drawing showing air dams placed along edges of a sheet of material to minimize air flow from under the edge of the material.

As shown in FIG. 6, the present invention includes a plurality of air dams 190. Each air dam 190 may be placed along an edge of the sheet of material 143 to minimize air flow into openings 122 from under the edge of the sheet of material 143. Air dams 190 may be made of lightweight aluminum or other metal. A set of air dams 190 may be used, with each set corresponding to a different sizes sheet of material 143. Air dams 190 may be placed adjacent to a sheet of material 143 that is not completely flat or is slightly curled up at the edges. Air dams 190 disrupt the air flow around the edges of the sheet of material 143 such that the vacuum source is able to pull the sheet of material 143 more efficiently. This results in the sheet of material 143 being held flat due to the tighter seal which is formed.

Air dams 190 are used by first aligning the sheet of material 143 with registration pins 134. After the vacuum source is then turned on and the sheet of material 143 has some amount of suction on it, registration pins 134 are removed and air dams 190 are placed adjacent to the sheet of material 143. In an alternative embodiment, air dams 190 may be formed with grooves in the edges corresponding to registration pins 134. Thus, the registration pins 134 would not need to be removed prior to placement of air dams 190 adjacent to the sheet of material 143 because registration pins 134 would fit within the grooves in air dams 190.

Although the present invention and its advantages have been described in detail, it should be understood that various changes, substitutions and modifications can be made without departing from the spirit and scope of the invention as defined by the following claims.

What is claimed is:

1. A vacuum easel for releasably holding material thereon, comprising:

a corrugated panel having a first sheet and a second sheet with a plurality of corrugated ribs disposed between the first sheet and the second sheet;

a plurality of air flow channels formed between the first sheet and the second sheet by the respective corrugated ribs;

a plurality of openings formed in the first sheet to allow communication of air between the exterior of the first sheet and the respective air flow channels;

a manifold coupled to the air flow channels to communicate a source of vacuum with the air flow channels to draw air from the exterior of the vacuum easel through the openings and into the air flow channels;

the corrugated panel having a generally rectangular configuration with a generally air impervious enclosure formed around the perimeter of the corrugated panel between the first sheet and the second sheet; and the second sheet providing a generally air impervious barrier.

2. The vacuum easel of claim 1, further comprising the corrugated panel formed from plastic material.

3. The vacuum easel of claim 1, further comprising a frame formed around the perimeter of the vacuum easel.

4. The vacuum easel of claim 1, further comprising a conduit attached to the manifold for use in connecting the manifold with the source of vacuum.

5. The vacuum easel of claim 4, wherein the conduit comprises flexible material.

6. The vacuum easel of claim 4, further comprising the conduit coupled to the source of vacuum to draw air from the exterior of the vacuum easel through the openings, the air flow channels and the manifold.

7. The vacuum easel of claim 1, wherein the corrugated panel has a thickness in the range of one millimeter to twenty millimeters.

8. The vacuum easel of claim 1, further comprising a plurality of recesses operable to receive a set of registration pins to align the sheet of material with at least a subset of the openings.

9. The vacuum easel of claim 1, wherein the openings are arranged in a plurality of progressively larger zones, each sized to hold a sheet of material of a different size, further comprising an air barrier operable to be positioned in the manifold to selectively communicate the source of the vacuum with the openings of a selected zone to draw air from the exterior of the vacuum easel through the openings of the selected zone.

10. The vacuum easel of claim 9, further comprising a plurality of recesses operable to receive a set of registration pins to align the sheet of material with one of the zones.

11. The vacuum easel of claim 9, wherein at least a portion of the openings of a zone are arranged along the edges of the zone, corresponding to the edges of the sheet of material.

12. The vacuum easel of claim 9, further comprising:
the corrugated panel disposed between a first structure and a second structure;
the first structure disposed outwardly of the first sheet of the corrugated panel and having a configuration corresponding generally with the first sheet;
the second structure disposed outwardly of the second sheet of the corrugated panel and having a configuration corresponding generally with the second sheet; and
a plurality of openings formed in the first structure to allow communication of air between the exterior of the first structure and the openings in the first sheet to releasably hold a sheet of material on the first structure.

13. The vacuum easel of claim 12, further comprising:
the first structure and the second structure formed from relatively hard, stiff material as compared to the corrugated panel; and
the first structure providing a generally smooth exterior surface for the vacuum easel.

14. A vacuum easel for releasably holding a sheet of material thereon, comprising:
a corrugated panel having a first sheet and a second sheet with a plurality of corrugated ribs disposed between the first sheet and the second sheet;
a plurality of air flow channels formed between the first sheet and the second sheet by the respective corrugated ribs;
a plurality of openings formed in the first sheet to allow communication of air between the exterior of the first sheet and the respective air flow channels;
a manifold coupled to the air flow channels to communicate a source of vacuum with the air flow channels to draw air from the exterior of the vacuum easel through the openings and into the air flow channels; and
a plurality of air dams each operable to be placed along an edge of the sheet of material to minimize air flow into the openings from under the edge of the sheet of material.

15. A vacuum easel for releasably holding material thereon, comprising:
a panel having a first sheet and a second sheet with a plurality of walls disposed between the first and second sheets;
the walls defining a series of progressively larger air pathways between the first and second sheets;
a plurality of openings formed in the first sheet to allow communication of air between the exterior of the first sheet and the respective air pathways;
at least a subset of the openings associated with each of the air pathways; and a zone selector operable to selectively communicate a source of vacuum with at least one of the air pathways to draw air from the exterior of the vacuum easel through the openings associated with the selected air pathway.

16. The vacuum easel of claim 15, wherein each air pathway is inclusive of each smaller air pathway.

17. The vacuum easel of claim 15, wherein the openings associated with an air pathway are arranged to hold a sheet of material of a predefined size.

18. The vacuum easel of claim 17, wherein at least some of the openings associated with an air pathway are arranged to hold the sheet of material proximate to edges of the sheet of material.

19. The vacuum easel of claim 15, further comprising:
a plurality of corrugated ribs disposed between the first sheet and the second sheet;
a plurality of air flow channels formed between the first sheet and the second sheet by the respective corrugated ribs; and
a plurality of dividers each disposed across at least one air flow channel to form a wall of an air pathway.

20. The vacuum easel of claim 19, further comprising a transverse channel formed in a section of air flow channels blocked from the vacuum source by a divider to communicate the vacuum source with the section of air flow channels.

21. The vacuum easel of claim 15, the zone selector comprising:
a manifold coupled to the air pathways to allow the source of vacuum to communicate with the air pathways to draw air from the exterior of the vacuum easel through the openings and into the air pathways; and
an air barrier operable to be positioned in the manifold to selectively communicate the source of vacuum with at least one of the air pathways to draw air from the exterior of the vacuum easel through the openings associated with the selected air pathway.

22. The vacuum easel of claim 21, wherein the air barrier is a zoning rod operable to slide into the manifold to selectively communicate the source of vacuum with at least one of the air pathways to draw air from the exterior of the vacuum easel through the openings associated with the selected air pathway.

23. The vacuum easel of claim 21, wherein the air barrier comprises a plurality of zoning rods operable to slide into opposing ends of the manifold to selectively communicate the source of vacuum with at least one of the air pathways to draw air from the exterior of the vacuum easel through the openings associated with the selected air pathway.

24. The vacuum easel of claim 21, further comprising:
a first aperture in a side of the panel corresponding to the manifold;
a second aperture in an opposing side of the panel corresponding to the manifold; and
the air barrier comprising a first zoning rod adapted to slide snugly into the manifold through the first aperture and a second zoning rod adapted to slide snugly into the manifold through the second aperture.

25. A method of holding a sheet of material to an easel, comprising the steps of:
providing a substantially flat surface having a plurality of openings arranged into a series of progressively larger zones, each sized to hold a sheet of material of a predefined size;
providing a plurality of air pathways each associated with at least one zone of the substantially flat surface;

positioning a sheet of material over the openings of a zone sized to hold the sheet of material;

positioning an air barrier in a manifold coupled to the air pathways to selectively communicate a source of vacuum with the openings of the zone sized to hold the sheet of material; and applying a vacuum to the manifold to draw air through the openings of the zone sized to hold the sheet of material.

26. The method of claim 25, the step of positioning the air barrier comprising sliding the air barrier to a position in the manifold to communicate the vacuum source with only the air pathways associated with the openings of the zone sized to hold the sheet of material.

27. The method of claim 25, the step of positioning the sheet of material over the openings of the zone comprising the steps of:

placing a set of registration pins within a set of recesses in the substantially flat surface associated with the zone; and aligning the sheet of material against the registration pins to position the sheet of material over the openings of the zone.

28. The method of claim 25, further comprising the step of positioning a plurality of air dams along a plurality of edges of the sheet of material to minimize air flow into the openings of the zone from under the edges of the sheet of material.

29. A vacuum easel for releasably holding material thereon, comprising:

a panel having a first sheet and a second sheet with a plurality of corrugated ribs disposed between the first sheet and the second sheet;

a plurality of air flow channels formed between the first sheet and the second sheet by the respective corrugated ribs;

a plurality of dividers each disposed across at least one air flow channel to form a wall of an air pathway, the air pathways being progressively larger and inclusive of each smaller air pathway;

a plurality of transverse channels to each allow the vacuum source to communicate with sections of air pathways blocked by dividers that form walls of smaller, included air pathways;

a plurality of openings formed in the first sheet to allow communication of air between the exterior of the first sheet and the respective air pathways, at least a subset of the openings associated with each of the air pathways and arranged to hold a sheet of material of a predefined size;

a manifold coupled to the air pathways to allow the source of vacuum to communicate with the air pathways to draw air from the exterior of the vacuum easel through the openings and into the air pathways; and an air barrier operable to slide in the manifold to selectively communicate the source of vacuum with at least one of the air pathways to draw air from the exterior of the vacuum easel through the openings associated with the selected air pathway.

30. The vacuum easel of claim 29, further comprising:

the panel disposed between a first structure and a second structure;

the first structure disposed outwardly of the first sheet of the panel and having a configuration corresponding generally with the first sheet;

the second structure disposed outwardly of the second sheet of the panel and having a configuration corresponding generally with the second sheet;

a plurality of openings formed in the first structure to allow communication of air between the exterior of the first structure and the openings in the first sheet to releasably hold a sheet of material on the first structure;

the first structure and the second structure formed from relatively hard, stiff material as compared to the panel; and the first structure providing a generally smooth exterior surface for the vacuum easel.

31. The vacuum easel of claim 29, further comprising a plurality of air dams each operable to be placed along a plurality of edges of the sheet of material to minimize air flow into the openings from under the edges of the sheet of material.

32. The vacuum easel of claim 29, further comprising a plurality of recesses operable to receive a set of registration pins to align the sheet of material with at least a subset of the openings.

* * * * *